(12) United States Patent
Hwang et al.

(10) Patent No.: US 11,839,610 B2
(45) Date of Patent: Dec. 12, 2023

(54) METHOD FOR INHIBITING INFECTION OF SARS-COV-2 IN A SUBJECT

(71) Applicant: Chang Gung University of Science and Technology, Taoyuan (TW)

(72) Inventors: Tsong-Long Hwang, Taoyuan (TW); Yu-Li Chen, Taoyuan (TW); Yu-Chia Chang, Taoyuan (TW)

(73) Assignees: CHANG GUNG UNIVERSITY OF SCIENCE AND TECHNOLOGY, Taoyuan (TW); CHANG GUNG UNIVERSITY, Taoyuan (TW)

( * ) Notice: Subject to any disclaimer, the term of this patent is extended or adjusted under 35 U.S.C. 154(b) by 0 days.

(21) Appl. No.: 17/806,274

(22) Filed: Jun. 10, 2022

(65) Prior Publication Data

US 2023/0321078 A1 Oct. 12, 2023

(30) Foreign Application Priority Data

Apr. 7, 2022 (TW) ................. 111113312

(51) Int. Cl.
*A61K 31/472* (2006.01)
*A61P 31/14* (2006.01)
*C12N 9/48* (2006.01)
*A61K 36/18* (2006.01)

(52) U.S. Cl.
CPC ............ *A61K 31/472* (2013.01); *A61K 36/18* (2013.01); *A61P 31/14* (2018.01); *C12N 9/485* (2013.01); *C07K 2319/30* (2013.01); *C12Y 304/17023* (2013.01)

(58) Field of Classification Search
CPC ........ A61K 31/472; A61K 36/18; A61P 31/14
See application file for complete search history.

(56) References Cited

U.S. PATENT DOCUMENTS

2011/0105755 A1* 5/2011 Carroll ............... C07D 491/147
546/35

OTHER PUBLICATIONS

Kim et al. "Natural Bis-Benzylisoquinoline alkaloids-Tetrandrine, Fangchinoline, and cepharanthine, inhibit human coronavirus OC43 infection of MRC-5 human lung cells," Biomolecules, 2019, 9, 696 (Year: 2019).*
Ruan et al. ("SARS-CoV-2 and SARS-CoV: virtual screen of potential inhibitors targeting RNA-dependent RNA polymerase activity (NSP12)," Medical Virology, 2021, 93: 389-400), (Year: 2021).*
Alexandar et al. "A comprehensive review on Covid-19delta variant," International J. Pharmacology and Clinical Research, 2021, vol. 5, Issue 2, pp. 83-85 (Year: 2021).*
Semwal et al. "The genus *Stephania* (Menispermaceae): Chemical and Pharmacological perspectives," J. Ethnopharmacology, 2010, 132, 369-383. (Year: 2010).*
"Menispermaceae" Wikipedia. https://en.wikipedia.org/wiki/Menispermaceae (Year: 2023).*
Huang et al. "Clinical features of patients infected with 2019 novel coronavirus in Wuhan, China," The Lancet, 2020, vol. 395, pp. 497-506, (Year: 2020).*

* cited by examiner

*Primary Examiner* — Shengjun Wang
(74) *Attorney, Agent, or Firm* — Hannah Tien

(57) ABSTRACT

A method for inhibiting infection of SARS-CoV-2 in a subject is provided, comprising administering an effective amount of plant extract, wherein the plant extract comprises an alcohol extract of the herbal of Menispermaceae, wherein the herbal of Menispermaceae is *Stephania cepharantha* or *Stephania tetrandra*.

6 Claims, 3 Drawing Sheets

METHOD FOR INHIBITING INFECTION OF SARS-COV-2 IN A SUBJECT

FIELD OF THE INVENTION

The present invention relates to a method for inhibiting infections caused by SARS-CoV-2 in a subject, particularly by using an alcohol extract of a herb of Menispermaceae to inhibit infections caused by SARS-CoV-2 in a subject.

BACKGROUND OF THE INVENTION

Severe acute respiratory syndrome coronavirus 2 (SARS-CoV-2) is a new type of coronavirus discovered in 2019, belonging to the genus of Betacoronavirus in the family of Coronaviridae. This virus is an enveloped positive-strand single-stranded RNA virus, the full-length genome is about 29.7 kb, and it is the seventh known coronavirus that can infect humans. The primary route of transmission of this virus is the respiratory tract, the virus enters cells through binding of spike proteins on the viral particle membrane and the angiotensin-converting enzyme 2 (ACE2) on a host cell, and the human organs can be infected include the lungs, heart, kidneys, and other human organs where ACE2 is widely distributed.

SARS-CoV-2 has a high transmission rate. When it enters the respiratory tract and infects lung tissues, inflammatory responses are induced, causing damages to the lung tissues, forming Severe special infectious pneumonia (COVID-19), and eventually developing the acute respiratory distress syndrome with a high mortality rate. It has become a global infectious disease, and new drugs against COVID-19 infections are being actively developed around the world, and blocking the binding of spike proteins to ACE2 is an important strategy for research and development of anti-SARS-CoV-2 drugs.

Natural compounds are advantageous for their abundant supplies and diverse skeletons, and they are important bases for drug development. From 1981 till 2019, nearly half of the new FDA-approved drugs were derived from natural products or their derivatives, for example, cocaine-derived narcotics, morphine-derived analgesics, vincristine, doxorubicin and paclitaxel for treating cancers, and fungus-derived penicillin as antibiotics. Therefore, the present invention actively studies to determine which natural compounds have the potential to be developed as novel drugs against COVID-19.

SUMMARY OF THE INVENTION

The present invention is a method for inhibiting infections caused by SARS-CoV-2 in a subject, comprising administering an effective amount of plant extract, wherein the plant extract comprises an alcohol extract of the herb of Menispermaceae.

DETAILED DESCRIPTION OF THE INVENTION

Figure 1:
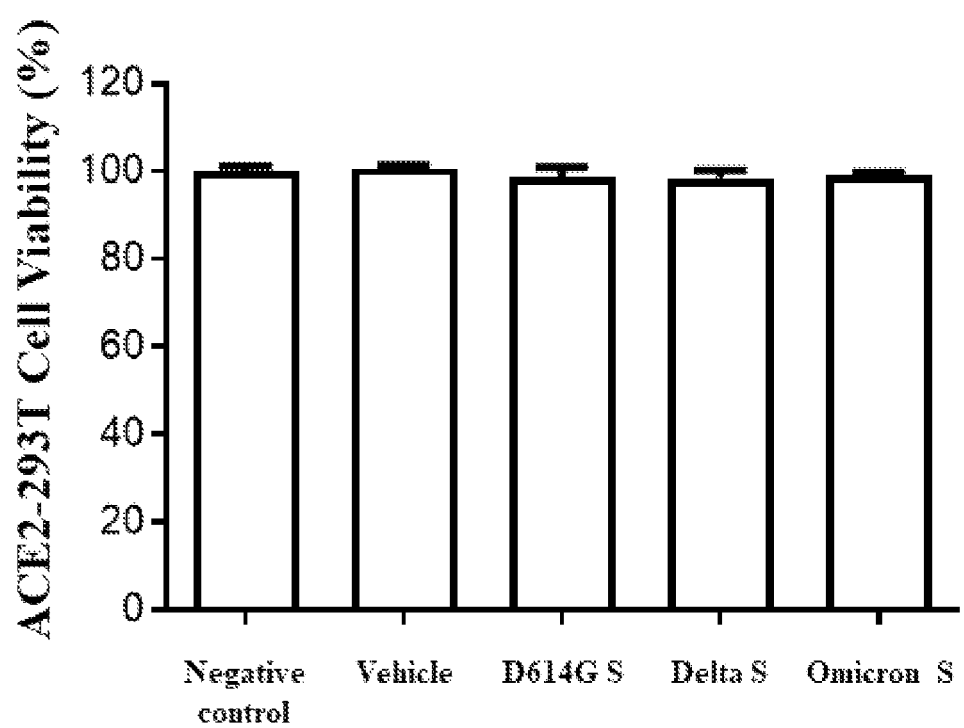
FIG. 1 shows the effect of pseudoviruses on the cell viability of the ACE2-293T cells.

The present invention is a method for inhibiting infections caused by SARS-CoV-2 in a subject, comprising administering an effective amount of plant extract, wherein the plant extract comprises an alcohol extract of the herb of Menispermaceae.

The present invention discovers that the alkaloid compounds contained in *Stephania cepharantha* and *Stephania tetrandra* in the family of Menispermaceae have the ability to inhibit viral infections and anti-inflammatory effect.

In the present invention, wherein the herbal alcohol extract is an ethanol extract.

Preferably, the herbal alcohol extract is an alkaloid concentrated layer extract of the ethanol extract.

In one embodiment, the herbal alcohol extract is a bisbenzylisoquinoline alkaloid.

In a more preferred embodiment, the herbal alcohol extract refers to Fangchinoline, Cepharanoline or Cycleanine.

In a more preferred embodiment, the herbal alcohol extract of the present invention inhibits the novel coronavirus infection of the subject through blocking the binding of spike proteins on the novel coronavirus and the angiotensin-converting enzyme 2 on the cells of the subject.

The novel coronavirus referred to in the present invention is the SARS-CoV-2 D614G variant, the SARS-CoV-2 Delta variant or the SARS-CoV-2 Omicron variant. More preferably, the novel coronavirus referred to in the present invention is the Delta variant. Most preferably, the novel coronavirus referred to in the present invention is the Omicron variant.

In the present invention, the subject referred to in the present invention is a human or a mammal.

DESCRIPTION OF EMBODIMENTS

One skilled in the art readily appreciates that the present invention is well adapted to carry out the objects and obtain the ends and advantages mentioned, as well as those inherent therein. The compositions, processes and methods for producing them, and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

Natural Compounds

A preliminary screen was conducted in the present invention by using a set of pseudoviruses screening system combined with computer molecular simulation computation to calculate, by virtual screening, the affinity of a compound and the spike protein receptor binding site from a database containing natural compounds, then pseudovirus assays were used to test the ability of the compounds for inhibiting spike protein-mediated viral infections. The present invention preliminarily discovered that the alkaloid compounds found in abundance in *Stephania cepharantha* and *Stephania tetrandra* of the Menispermaceae have the ability of inhibiting viral infections.

Therefore, the present invention carried out subsequent researches with an indigenous plant in Taiwan—*Stephania cepharantha*.

In the present invention, after extraction of *Stephania cepharantha* with ethanol, chemical composition analysis and activity evaluation were carried out. Fangchinoline was found in the alkaloid concentrated layer in the ethanol extract. Cepharanoline and Cycleanine were also presented in *Stephania cepharantha*. These compounds are bis-benzylisoquinoline alkaloids.

Pseudoviruses

The VSV-G pseudovirus (clone name: S3w.Fluc.Ppuro) of the control group and the VSV-G pseudovirus expressing spike proteins of SARS-CoV-2 (clone name: nCoV-S-Luc-D614G, nCoV-S-Luc-B.1.617.2 and nCoV-S-Luc-B.1.1.529) were purchased from the RNAiCore Core Facility of Academia Sinica, Taiwan.

Among them, the nCoV-S-Luc-D614G pseudovirus expressed the spike proteins of the SARS-CoV-2 D614G variant (hereinafter referred to as the D614G S protein), the nCoV-S-Luc-B.1.617.2 pseudovirus expressed the spike proteins of the SARS-CoV-2 Delta variant (hereinafter referred to as Delta S protein), nCoV-S-Luc-B.1.1.529 pseudovirus expressed the spike proteins of SARS-CoV-2 Omicron variant (hereinafter referred to as Omicron S protein).

SARS-CoV-2 Pseudovirus Infection Assay

First, the HEK-293T cells that overexpressed hACE-2 protein (hereinafter referred to as ACE2-293T cells) were seeded in a 96-well cell culture plate at the concentration of $1 \times 10^4$ cells per well, and cultivated at 37° C. in a 5% $CO_2$ incubator.

The ACE2-293T cells were divided into a Negative control group (untreated), a Vehicle group (provided with HBSS), a D614G S protein group (provided with 0.5 R.I.U. of D614G S protein pseudovirus), a Delta S protein group (provided with 0.5 R.I.U. Delta S protein pseudovirus) and an Omicron S protein group (provided with 0.5 R.I.U. of Omicron S protein pseudovirus).

The pseudovirus at the concentration of 0.5 relative infection unit (R.I.U.) per cell (0.5 R.I.U./cell; that is, $5 \times 10^3$ RIU/well) were pre-treated at 37° C. with different concentrations of antiviral agents in DMEM media containing 10% fetal bovine serum (FBS) for 1 hour. Subsequently, the media of the ACE2-293T cells of the D614G S protein group, the Delta S protein group, and the Omicron S protein group were replaced with the pretreated pseudovirus solution and cultivated for 24 hours. The Vehicle group, in which the virus solution was replaced with HBSS, was treated with the same treatment steps.

The infection effect of VSVG, D614GS, Delta S and Omicron S pseudo-lentiviral solutions were 2,682 R.I.U./μL, 737 R.I.U./μL, 190 R.I.U./μL and 1,070 R.I.U./μL, respectively.

After the host cells were infected, the luciferase activity was measured with a Luciferase Assay System (E2520, Promega) and recorded by a fluorometric reader. Briefly, the luciferase activity of the ACE2-293T cells was assayed by using the cell lysates and a luciferase substrate according to the manufacturer's instructions.

Pseudovirus Cytotoxicity Analysis

The cell viability of the ACE2-293T cells of the Negative control group (untreated), the Vehicle group (provided with HBSS), the D614G S protein group (provided with 0.5 R.I.U. of D614G S protein pseudovirus), the Delta S protein group (provided with 0.5 R.I.U. of Delta S protein pseudovirus) and the Omicron S protein group (provided with 0.5 R.I.U. of Omicron S protein pseudovirus) were tested 24 hours after being treated. The results are shown in Table 1 and FIG. 1, there are no significant differences in the cell viability of the cells in each group.

TABLE 1

| Groups | Cell Viability (%) |
| --- | --- |
| Negative control group | 100.00 ± 1.12 |
| Vehicle group | 100.77 ± 0.72 |
| D614G S | 98.06 ± 2.38 |
| Delta S | 98.48 ± 1.18 |
| Omicron S | 99.19 ± 0.61 |

Data are presented as means ± standard deviations (n = 3)
Compared to the Negative control group Viral Infection Inhibition Test First, the pseudovirus assay was used to test whether or not *Stephania cepharantha* (SC) and *Stephania tetrandra* (ST) were able to inhibit viral infections mediated by the SARS-CoV-2 spike proteins, and the pseudovirus expressed spike proteins of different variants were evaluated.

After *Stephania cepharantha* (SC) and *Stephania tetrandra* (ST) were extracted with ethanol, the alkaloid concentrated layer was further separated, and then the ethanol extract and the alkaloid concentrated layer of *Stephania cepharantha* (SC) and *Stephania tetrandra* (ST) were formulated into high-concentration drug solutions (1, 3, 10, and 30 mg/mL) with dimethyl sulfoxide (DMSO).

The viral solution was added to 10% FBS DMEM medium to formulate a viral solution having the concentration of $5 \times 10^4$ R.I.U./ml. 1 mL viral solution was removed and added to 1 μL of DMSO or 1 μL of a drug solution of a specified concentration, and the virus and the extract were allowed to react at 37° C. for 1 hour.

The ACE2-293T cells were seeded in 96-well plates at a cell density of $1 \times 10^4$ cells/well, and cultivated at 37° C. in a DMEM containing 10% of FBS and 10 μg/mL of blasticidin.

After being cultivated for 10 hours to allow the cells to attach, 100 μL of the drug-virus mixture solution was added to infect the cells. After 24 hours of cultivation at 37° C., the luciferase activity in the 96-well plate was quantified according to the manufacturer's instruction to show the course of viral infection.

The results are shown in Table 2. The 50% inhibitory concentrations ($IC_{50}$) of the ethanol extract of *Stephania cepharantha* (SC-EtOH) against the D614G S protein group, the Delta S protein group and the Omicron S protein group were 24.64±0.21 μg/mL, 16.01±1.22 μg/mL, and 13.20±1.63 μg/mL, respectively. The 50% inhibitory concentrations ($IC_{50}$) of the ethanol extract of *Stephania tetrandra* (ST-EtOH) against the D614G S protein group, Delta S protein group and the Omicron S protein group, were 11.64±1.81 μg/mL, 16.06±0.60 μg/mL and 8.29±1.50 μg/mL, respectively.

It is worth noting that the 50% inhibitory concentrations of the alkaloid concentrated layer of the *Stephania cepharantha* ethanol extract (SC-EtOH-alkaloid) against the D614G S protein group, the Delta S protein group and the Omicron S protein group were 3.79±0.06 μg/mL, 4.44±0.03 μg/mL and 1.20±0.17 μg/mL.

The 50% inhibitory concentrations of the alkaloid concentrated layer of the *Stephania tetrandra* ethanol extract (SC-EtOH-alkaloid) against the D614G S protein group, the Delta S protein group and the Omicron S protein group are 1.40±0.04 μg/mL, 1.57±0.01 μg/mL and 0.55±0.03 μg/mL, respectively.

Based on these results, it is known that the main components of *Stephania cepharantha* and *Stephania tetrandra* that inhibit the viral infections mediated by the SARS-CoV-2 spike protein exist in the alkaloids.

TABLE 2

| Herbal extract | 50% inhibitory concentrations (IC$_{50}$) for viral infection | | |
|---|---|---|---|
| | D614G | Delta | Omicron |
| SC-EtOH | 24.64 ± 0.21 | 16.01 ± 1.22 | 13.20 ± 1.63 |
| SC-EtOH-alkaloid | 3.79 ± 0.06 | 4.44 ± 0.03 | 1.20 ± 0.17 |
| ST-EtOH | 11.64 ± 1.81 | 16.06 ± 0.60 | 8.29 ± 1.50 |
| ST-EtOH-alkaloid | 1.40 ± 0.04 | 1.57 ± 0.01 | 0.55 ± 0.03 |

50% inhibitory concentration (IC$_{50}$, µg/mL), n = 3

In order to further explore which alkaloid compound had the strongest potency to inhibit the viral infections mediated by the SARS-CoV-2 spike protein, the present invention conducted the subsequent researches with an indigenous Menispermaceae plant in Taiwan—*Stephania cepharantha*.

After *Stephania cepharantha* was extracted with ethanol, chemical composition analysis and activity evaluation were conducted, and Fangchinoline was discovered in the alkaloid concentrated layer of the ethanol extract, in addition, Cepharanoline or Cycleanine were also contained in *Stephania cepharantha*. The above compounds all had the ability to inhibit viral infections.

The compounds Fangchinoline, Cepharanoline and Cycleanine were formulated into DMSO solutions of different concentrations with DMSO.

Preparation of virus solution: the virus solution was added in 10% FBS DMEM to afford a virus concentration of 5×10$^4$ R.I.U./mL. 1 mL of virus solution was removed and added to 1 µL of DMSO or the DMSO solution of a specified compound, and the virus and the drug were allowed to react at 37° C. for 1 hour.

The ACE2-293T cells were seeded in a 96-well plate at a cell density of 1×10$^4$ cells/well and cultivated in DMEM containing 10% FBS and 10 µg/mL of blasticidin at 37° C.

After 10 hours of incubation to allow the cells to attach, 100 µL of the drug-virus mixture solution was added to infect the cells.

After 24 hours of incubation at 37° C., the activities of these compounds against the D614G S protein group, the Delta S protein group, and the Omicron S protein group were quantified by conducting quantification of luciferase activity in the 96-well plate according to the manufacturer's instructions to test the activity of the luciferase in the cells to show the levels of viral infections. The method of calculation was to take the value of the luciferase activity of the Control group as 100%, and the levels of infection were determined by subtracting the value of the luciferase activity of the Control Group from the value of the luciferase activity of each variant S protein group. The results are shown in Table 3.

TABLE 3

| | | D614G | | | Delta | | | Omicron | |
|---|---|---|---|---|---|---|---|---|---|
| | Conc. (µM) | Ave. | S.D. | Conc. (µM) | Ave. | S.D. | Conc. (µM) | Ave. | S.D. |
| Fangchinoline | 0 | 100 | 8.93 | 0 | 100 | 6.4 | 0 | 100 | 2.72 |
| | 1 | 81.22 | 2.49 | 1 | 64.54 | 0.82 | 0.3 | 83.62 | 4.85 |
| | 10 | 29.41 | 10.25 | 5 | 27.89 | 1.97 | 1 | 59.93 | 1.18 |
| | | | | 10 | 7.13 | 0.2 | 3 | 29.3 | 3.06 |
| | | | | | | | 10 | 11.55 | 1.08 |
| Cepharanoline | 0 | 100 | 8.93 | 0 | 100 | 6.4 | 0 | 100 | 0.98 |
| | 0.1 | 72.97 | 4.13 | 0.1 | 89.65 | 8.69 | 0.3 | 85.07 | 6.45 |
| | 1 | 39.14 | 2.4 | 1 | 64.01 | 3.97 | 1 | 57.89 | 2.37 |
| | 10 | −20.02 | 0.81 | 10 | −3.64 | 1.23 | 3 | 27.05 | 1.82 |
| | | | | | | | 10 | 7.32 | 1.2 |
| Cycleanine | 0.1 | 77.42 | 5.33 | 0.1 | 118.65 | 0.84 | 0 | 100.9 | 3.4 |
| | 1 | 67.04 | 2.87 | 1 | 88.48 | 13.32 | 0.3 | 71.54 | 3.05 |
| | 10 | −19.92 | 0.96 | 10 | −3.84 | 0.66 | 1 | 29.01 | 2.33 |
| | | | | | | | 3 | 13.53 | 2.9 |
| | | | | | | | 10 | 8.41 | 1.64 |

Conc.: Concentration;
Ave.: Average;
S.D.: Standard deviation

Figure 2:
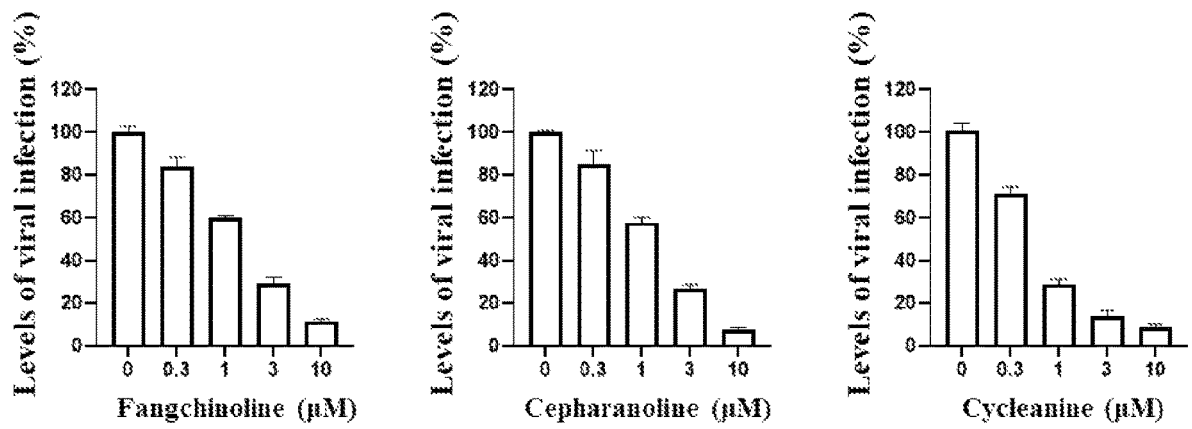
FIG. 2 shows the potency of each alkaloid compound of the present invention on the effect of the infection of the Omicron variant S protein pseudovirus.
Figure 3:
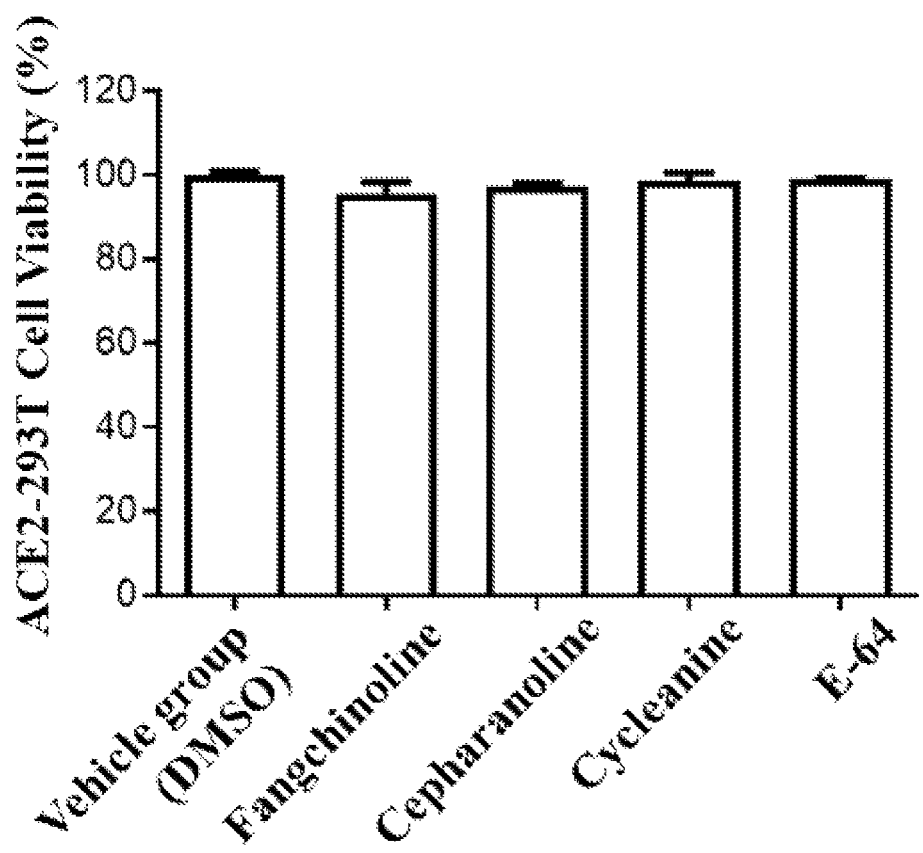
FIG. 3 shows the effect of each alkaloid compound of the present invention on the cell viability of the ACE2-293T cells.

Taking the Omicron variant S protein pseudovirus as a representative, the infection inhibition trend of each compound with respect to the Omicron variant S protein pseudovirus could be observed (FIG. 2).

The 50% inhibitory concentration (IC$_{50}$) of its antiviral S protein was further calculated, and the results are shown in Table 4. The IC$_{50}$ of E-64 compound group (a compound that was considered to be capable of inhibiting SARS-CoV-2 infection by current researches; Control group) against the D614G S protein group, the Delta S protein group and the Omicron S protein group were 23.12±0.63 µM, 23.06±1.30 µM and 22.69±1.28 µM, respectively.

TABLE 4

| Alkaloid compounds | 50% inhibitory concentrations (IC$_{50}$) for viral infection | | |
|---|---|---|---|
| | D614G | Delta | Omicron |
| Fangchinoline | 4.64 ± 0.96 | 1.82 ± 0.02 | 1.44 ± 0.06 |
| Cepharanoline | 0.48 ± 0.09 | 1.64 ± 0.18 | 1.31 ± 0.07 |
| Cycleanine | 0.23 ± 0.02 | 2.21 ± 0.50 | 0.53 ± 0.03 |
| E-64 | 23.12 ± 0.63 | 23.06 ± 1.30 | 22.69 ± 1.28 |

50% inhibitory concentration (IC5$_{50}$, µM), n = 3

The 50% inhibitory concentration (IC$_{50}$) of its antiviral S protein was further calculated, and the results were compared to the E-64 compound group. The 50% inhibitory concentration (IC$_{50}$) of Fangchinoline against the D614G S protein group was 4.64±0.96 μM, and the 50% inhibitory concentration ($IC_{50}$) against the Delta S protein group was 1.82±0.02 μM, and the 50% inhibitory concentration ($IC_{50}$) against the Omicron S protein group was 1.44±0.06 μM; the 50% inhibitory concentration ($IC_{50}$) of Cepharanoline against the D614G S protein group was 0.48±0.09 μM, the 50% inhibitory concentration ($IC_{50}$) for the Delta S protein group was 1.64±0.18 μM, and the 50% inhibitory concentration ($IC_{50}$) for the Omicron S protein group was 1.31±0.07 μM; the 50% inhibitory concentration ($IC_{50}$) of Cycleanine against the D614G S protein Group was 0.23±0.02 μM, the 50% inhibitory concentration ($IC_{50}$) for the Delta S protein group was 2.21±0.50 μM, and the 50% inhibitory concentration ($IC_{50}$) for the Omicron S protein group was 0.53±0.03 μM.

These results indicated that Fangchinoline, Cepharanoline and Cycleanine had the ability of broadly inhibiting different SARS-CoV-2 variant spike protein-mediated viral infections.

Alkaloid Cytotoxicity Analysis

The ACE2-293T cells were seeded in a 96-well plate at a density of $1\times10^4$ cells/well, and cultured at 37° C., 5% $CO_2$ for 10 hours. 10 mM solutions of Fangchinoline, Cepharanoline and Cycleanine in DMSO were prepared. 1 mL of 10% FBS DMEM medium without phenol red indicator was removed and added to 1 μL of DMSO or 10 mM of alkaloid drug-DMSO solution to formulate a one-thousandth diluted drug-DMEM medium solution. After removing the culture medium solution of the ACE2-293T cells, 100 μL of DMEM medium containing the drug was added, after being cultured for 24 hours, 20 μL of WST-1 compound was added, after allowing to be reacted at 37° C. in the dark for four hours, an enzyme immunoassay analyzer (ELISA reader) was used to read the absorbance at wavelength 450 nm, and a comparison was made with the control group which was set as 100%.

To further investigate whether alkaloid compounds such as Fangchinoline, Cepharanoline and Cycleanine were cytotoxic to the ACE2-293T cells, the present invention conducted a cytotoxicity analysis with a dose of 10 uM. The results showed that Fangchinoline, Cepharanoline and Cycleanine caused no damages to the ACE2-293T cells (Table 5 and FIG. 3). The results further showed that Fangchinoline, Cepharanoline and Cycleanine were able to broadly inhibit different SARS-CoV-2 variant spike protein-mediated viral infections.

TABLE 5

| Groups | Cell Viability (%) |
|---|---|
| Vehicle group | 100.00 ± 0.83 |
| Fangchinoline | 95.56 ± 2.82 |
| Cepharanoline | 97.24 ± 0.87 |
| Cycleanine | 98.59 ± 1.98 |
| E-64 | 99.16 ± 0.13 |

Data are presented as means ± standard deviations (n = 3)
Compared to the Vehicle group (DMSO)

The present invention demonstrated that *Stephania cepharantha* and *Stephania tetrandra* of the Menispermaceae had the ability to broadly inhibit different SARS-CoV-2 variant spike protein-mediated viral infections.

What is claimed is:

1. A method for inhibiting infection caused by SARS-CoV-2 in a subject, comprising administering an effective amount of plant extract, wherein the plant extract comprises an alcohol extract of Menispermaceae, and wherein the alcohol extract of Menispermaceae is Fangchinoline, Cepharanoline or Cycleanine.

2. The method of claim 1, wherein the herb of Menispermaceae is *Stephania cepharantha* or *Stephania tetrandra*.

3. The method of claim 1, wherein the plant alcohol extract inhibits infections caused by SARS-CoV-2 through blocking a biding of spike proteins of the SARS-CoV-2 and angiotensin-converting enzyme 2 (ACE2) of cells of the subject.

4. The method of claim 1, wherein the SARS-CoV-2 is a D614G variant, a Delta variant, or an Omicron variant.

5. The method of claim 1, wherein the SARS-CoV-2 is the Delta variant or the Omicron variant.

6. The method of claim 1, wherein the subject is a human or a mammal.

* * * * *